US00PP19839P2

(12) United States Plant Patent
Holtmaat

(10) Patent No.: US PP19,839 P2
(45) Date of Patent: Mar. 24, 2009

(54) ***ASTILBE* PLANT NAMED 'DELFT LACE'**

(50) Latin Name: *Astilbe hybrid*
Varietal Denomination: Delft Lace

(75) Inventor: Henricus Maria Joseph Holtmaat, Zuidwolde (NL)

(73) Assignee: Maatschap Holtmaat, Zuidwolde (NL)

( * ) Notice: Subject to any disclaimer, the term of this patent is extended or adjusted under 35 U.S.C. 154(b) by 0 days.

(21) Appl. No.: 11/983,722

(22) Filed: Nov. 12, 2007

(51) Int. Cl.
*A01H 5/00* (2006.01)

(52) U.S. Cl. ..... Plt./407
(58) Field of Classification Search ..... Plt./407
See application file for complete search history.

*Primary Examiner*—Wendy C. Haas
(74) *Attorney, Agent, or Firm*—C. A. Whealy

(57) ABSTRACT

A new and distinct cultivar of *Astilbe* plant named 'Delft Lace', characterized by its upright and sturdy plant habit; strong and healthy dark-green colored foliage; freely flowering habit; dark pink-colored flowers; and good garden performance.

2 Drawing Sheets

Botanical designation: *Astilbe hybrid.*
Cultivar denomination: 'DELFT LACE'.

BACKGROUND OF THE INVENTION

The present invention relates to a new and distinct cultivar of *Astilbe,* botanically known as *Astilbe hybrid* and hereinafter referred to by the name 'Delft Lace'.

The new *Astilbe* is a product of a planned breeding program conducted by the Inventor in Zuidwolde, The Netherlands. The objective of the breeding program was to create new compact and sturdy *Astilbe* cultivars with numerous attractive flowers.

The new Astilbe originated from an open-pollination in 1998 in Zuidwolde, The Netherlands, of an unidentified selection of *Astilbe hybrid,* not patented, as the female, or seed, parent with an unknown selection of *Astilbe hybrid,* as the male, or pollen, parent. The new *Astilbe* was discovered and selected by the Inventor as a single flowering plant within the progeny of the stated open-pollination in a controlled environment in Zuidwolde, The Netherlands in 2001.

Asexual reproduction of the new *Astilbe* by divisions in a controlled environment in Zuidwolde, The Netherlands since 2004, has shown that the unique features of this new *Astilbe* are stable and reproduced true to type in successive generations.

SUMMARY OF THE INVENTION

The cultivar Delft Lace has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Delft Lace'. These characteristics in combination distinguish 'Delft Lace' as a new and distinct cultivar of *Astilbe:*

1. Upright and sturdy plant habit.
2. Strong and healthy dark green-colored foliage.
3. Freely flowering habit.

4. Dark pink-colored flowers.
5. Good garden performance.

Plants of the new *Astilbe* and the female parent selection differ primarily in flower coloration and plant height.

Plants of the new *Astilbe* can be compared to plants of the cultivar Key West, not patented. In side-by-side comparisons conducted in Zuidwolde, The Netherlands, plants of the new *Astilbe* and the cultivar Key West differed in the following characteristics:

1. Plants of the new *Astilbe* were taller and broader than plants of the cultivar Key West.
2. Plants of the new *Astilbe* had darker-colored leaves than plants of the cultivar Key West.
3. Plants of the new *Astilbe* had longer inflorescences than plants of the cultivar Key West.

BRIEF DESCRIPTION OF THE PHOTOGRAPHS

The accompanying colored photographs illustrate the overall appearance of the new *Astilbe,* showing the colors as true as it is reasonably possible to obtain in colored reproductions of this type. Colors in the photographs may differ slightly from the color values cited in the detailed botanical description which accurately describe the colors of the new *Astilbe.*

The photograph on the first sheet comprises a side perspective view of a typical flowering plant of 'Delft Lace' grown in a container.

The photograph at the top of the second sheet is a close-up view of typical flowers of 'Delft Lace'.

The photograph at the bottom of the second sheet is a close-up view of the upper surface of a typical leaf of 'Delft Lace'.

DETAILED BOTANICAL DESCRIPTION

The aforementioned photographs and following observations, measurements and values describe plants grown in containers in Zuidwolde, The Netherlands, under commercial practice during the summer autumn in an outdoor nursery with day temperatures ranging from 12° C. to 32° C. and night temperatures ranging from 6° C. to 18° C. Plants had been growing for about one year when the photographs and description were taken. In the following description, color references are made to The Royal Horticultural Society Colour Chart, 2001 Edition, except where general terms of ordinary dictionary significance are used.

Botanical classification: *Astilbe hybrid* cultivar Delft Lace.

Parentage:

*Female, or seed, parent.*—Unidentified selection of *Astilbe hybrid,* not patented.

*Male, or pollen, parent.*—Unknown selection of *Astilbe hybrid,* not patented.

Propagation:

*Type.*—By divisions.

*Time to initiate roots, summer.*—About 10 days at 22° C.

*Time to initiate roots, winter.*—About 20 days at 10° C.

*Time to produce a rooted plant.*—About six weeks at 20° C. to 25° C.

*Root description.*—Fibrous, medium in thickness; off-white in color.

*Rooting habit.*—Moderately branching.

Plant description:

*Plant form/habit.*—Herbaceous perennial. Upright and sturdy plant habit; roughly narrowly triangular. Flowering stems and leaves basal; dense and bushy growth habit; moderately vigorous growth habit. Freely flowering habit with numerous flowers on branched panicles.

*Growth rate.*—Moderate; from divisions, about 20 weeks are required to produce fully-grown flowering plants.

*Plant height* (*soil level to top of foliar plane*).—About 26 cm.

*Plant height* (*soil level to top of inflorescence.*).—About 65.5 cm.

*Plant width* (*spread*).—About 51.5 cm.

*Stem description.*—Length: About 24.1 cm. Diameter: About 4 mm. Internode length: About 6.1 cm. Strength: Strong. Texture: Sparsely pubescent. Color: Darker than 183A.

Foliage description:

*Arrangement.*—Alternate; biternately compound.

*Leaf length* (*excluding petiole*).—About 18.1 cm.

*Leaf width.*—About 21.1 cm.

*Lateral leaflet length.*—About 4.8 cm.

*Lateral leaflet width.*—About 2.9 cm.

*Terminal leaflet length.*—About 6.5 cm.

*Terminal leaflet width.*—About 4.6 cm.

*Lateral and terminal leaflet shape.*—Ovate.

*Lateral and terminal leaflet apex.*—Narrowly acute.

*Lateral and terminal leaflet base.*—Attenuate with truncate tendencies.

*Lateral and terminal leaflet margin.*—Biserrate.

*Lateral and terminal leaflet texture, upper and lower surfaces.*—Sparsely pubescent; slightly rough.

*Lateral and terminal leaflet venation pattern.*—Pinnate.

*Lateral and terminal leaflet color.*—Developing leaves, upper surface: 143A to 143B. Developing leaves, lower surface: 143A. Fully expanded leaves, upper surface: Darker than 137A; venation, 138B. Fully expanded leaves, lower surface: 137C; towards the margins, between 178A and 183A; venation, 146C.

*Leaf petiole length.*—About 12.4 cm.

*Leaf petiole diameter.*—About 3 mm.

*Leaflet petiole length.*—About 4.2 cm.

*Leaflet petiole width.*—About 3 mm.

*Leaf and leaflet petiole texture, upper and lower surfaces.*—Smooth, glabrous.

*Leaf and leaflet petiole color, upper and lower surfaces.*—Towards the apex, 187A; towards the base, close to 144B.

Flower description:

*Flower type/habit.*—Numerous single rotate flowers arranged on branched panicles; flowers face upright, outward or downward depending on position on the panicle. Panicles narrowly conical in shape. Freely and uniformly flowering habit with about 750 flowers develop per inflorescence; typically 13 panicles develop per plant.

*Fragrance.*—Moderately fragrant; sweet.

*Natural flowering season.*—Continuously flowering for about six weeks during the summer and late summer in The Netherlands.

*Postproduction longevity.*—Flowers last about ten days on the plant. Flowers persistent.

*Flower buds.*—Height: About 2 mm. Diameter: About 1.5 mm. Shape: Broadly ovate. Color: 183B to 183C; towards the base, 144B.

*Inflorescence height.*—About 30.8 cm.

*Inflorescence diameter.*—About 27.7 cm.

*Flower diameter.*—About 7 mm.

*Flower depth.*—About 5 mm.

*Petals.*—Quantity per flower: Typically five in a single whorl. Length: About 4 mm. Lobe width: About 1 mm. Shape: Narrowly oblanceolate. Apex: Acute. Margin: Entire. Texture, upper and lower surfaces: Smooth, glabrous. Color: Developing petals, upper and lower surfaces: Close to 155D. Fully expanded petals, upper and lower surfaces: Close to 155D; color becoming closer to 155A with development.

*Sepals.*—Quantity per flower: Typically five in a single whorl, fused towards the base; campanulate calyx. Length: About 2 mm. Width: About 1.5 mm. Shape: Ovate. Apex: Acute. Margin: Entire. Texture, upper and lower surfaces: Smooth, glabrous. Color, developing sepals, upper and lower surfaces: Close to between 58A and 62D. Color, fully expanded sepals, upper and lower surfaces: Close to 63B; towards the base, close to 65D.

*Peduncles.*—Length: About 30.4 cm. Diameter: About 3 mm. Angle: Mostly erect. Strength: Strong. Texture: Densely pubescent. Color: 183A.

*Pedicels.*—Length: About 0.5 mm. Diameter: About 0.5 mm. Angle: About 45° from vertical. Strength: Moderately strong. Texture: Smooth, glabrous. Color: 65A.

*Reproductive organs.*—Stamens: Quantity per flower: Typically ten; anthers basifixed. Filament length: About 3 mm. Anther shape: Ovate. Anther length: About 0.3 mm. Anther color: Darker than 116A. Pollen amount: Scarce. Pollen color: Close to 155D. Pistils: Quantity per flower: Typically two. Pistil length: About 1 mm. Stigma shape: Club-shaped. Stigma color: 65D. Style length: About 0.9 mm. Style color: Close to 155A. Ovary color: Close to 155A.

*Seed/fruit.*—Seed and fruit development have not been observed.

Disease/pest resistance: Plants of the new *Astilbe* have not been noted to be resistant to pathogens and pests common to *Astilbe*.

Garden performance: Plants of the new *Astilbe* have been observed to have good garden performance and tolerate rain, wind and high temperatures of about 35° C. Plants of the new *Astilbe* have been observed to be hardy to USDA Zone 5.

It is claimed:

1. A new and distinct *Astilbe* plant named 'Delft Lace' as illustrated and described.

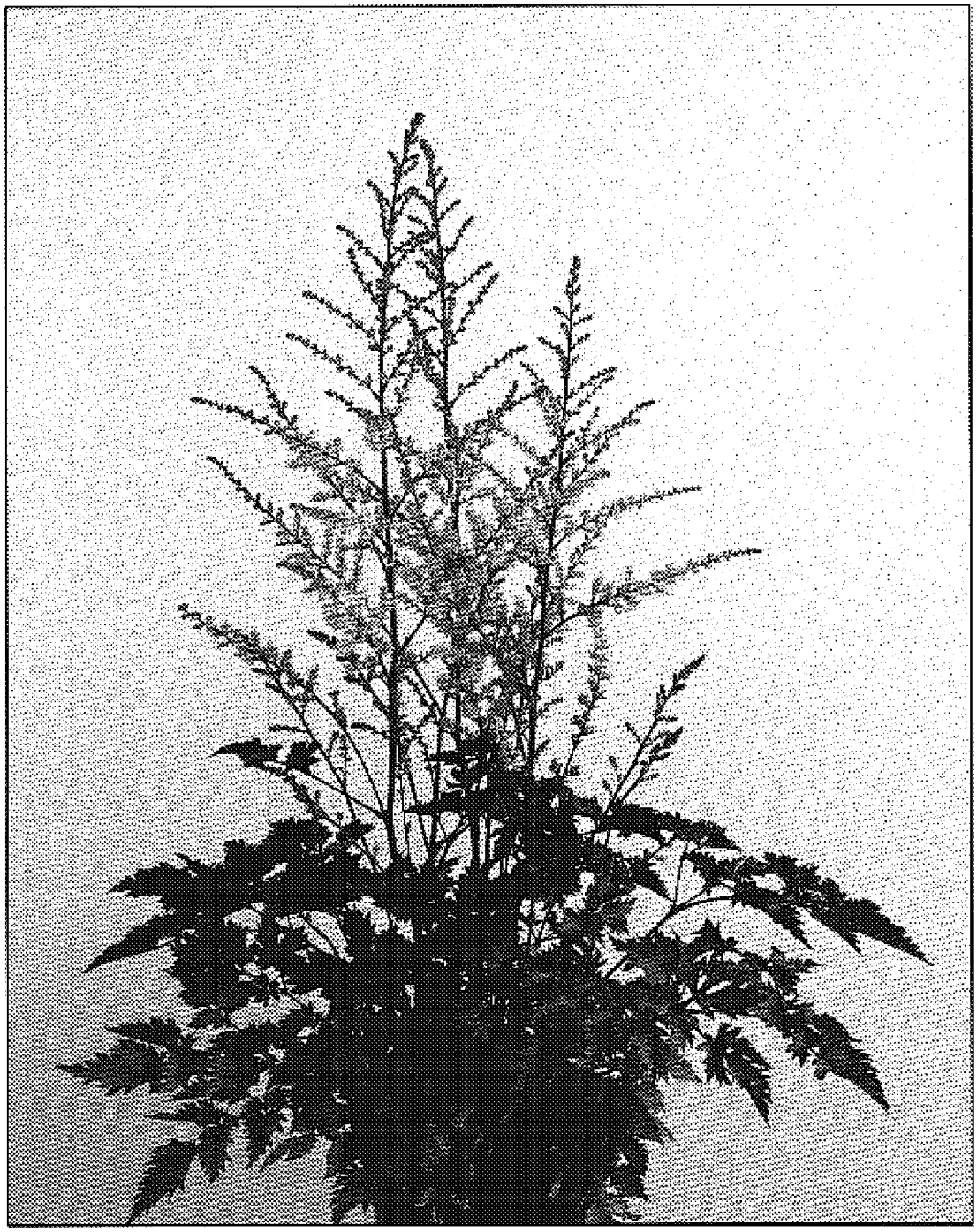

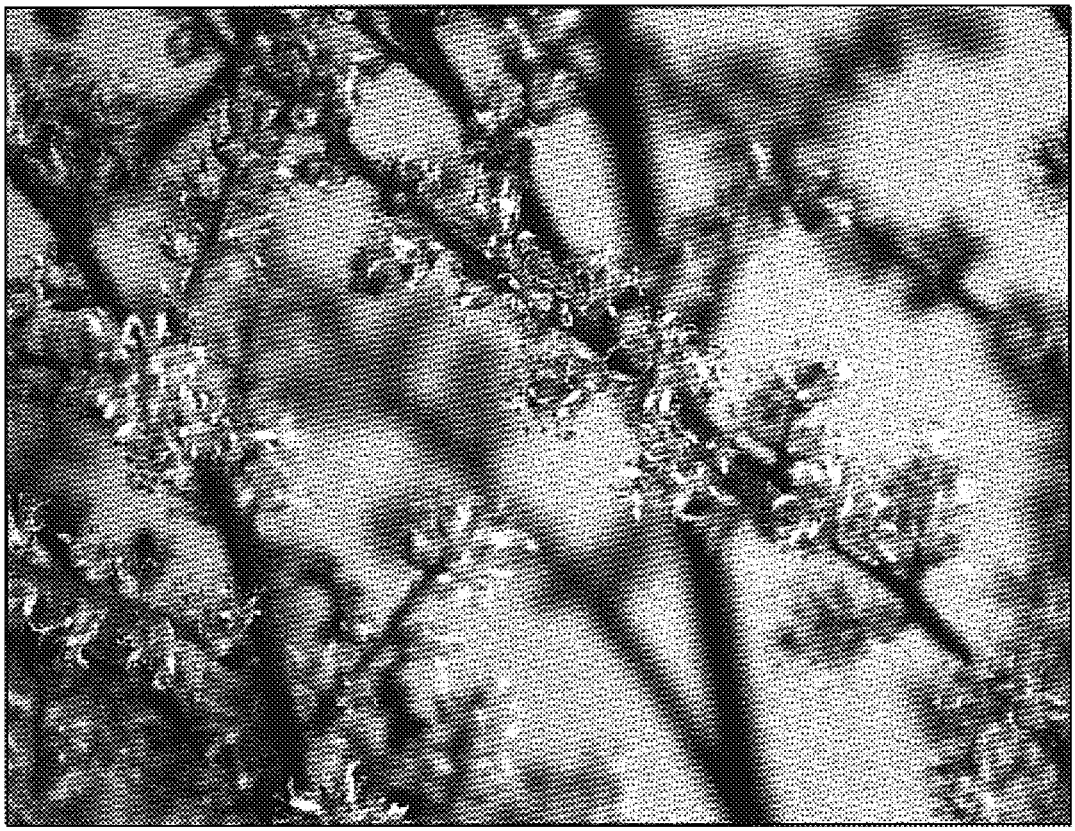
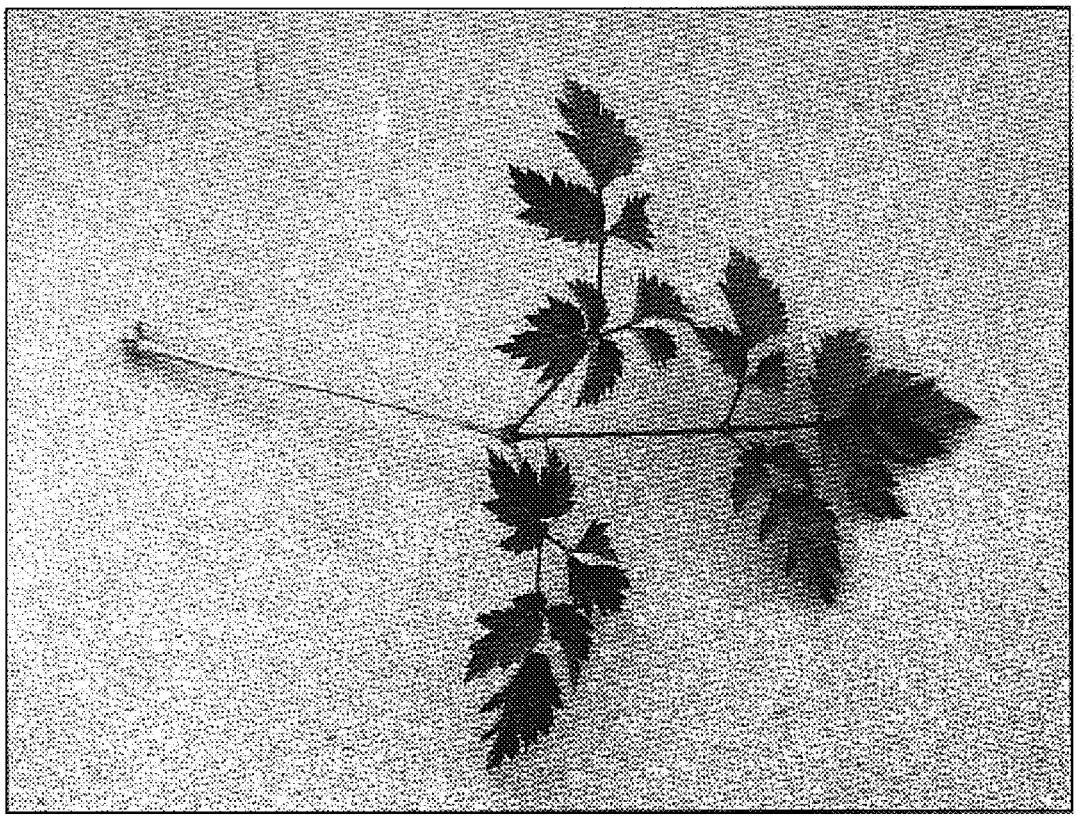

* * * * *